US008158780B2

(12) United States Patent
Phull et al.

(10) Patent No.: US 8,158,780 B2
(45) Date of Patent: Apr. 17, 2012

(54) PROCESSES FOR THE PREPARATION OF CICLESONIDE AND ITS CRYSTAL MODIFICATION

(75) Inventors: Manjinder Singh Phull, Maharashtra (IN); Dharmaraj Ramachandra Rao, Maharashtra (IN); Rajendra Narayanrao Kankan, Maharashtra (IN)

(73) Assignee: Cipla Limited, Mumbai (IN)

( * ) Notice: Subject to any disclaimer, the term of this patent is extended or adjusted under 35 U.S.C. 154(b) by 432 days.

(21) Appl. No.: 12/441,283

(22) PCT Filed: Sep. 18, 2007

(86) PCT No.: PCT/GB2007/003549
§ 371 (c)(1),
(2), (4) Date: Jun. 16, 2009

(87) PCT Pub. No.: WO2008/035066
PCT Pub. Date: Mar. 27, 2008

(65) Prior Publication Data
US 2010/0222572 A1    Sep. 2, 2010

(30) Foreign Application Priority Data

Sep. 19, 2006  (IN) .................... 1493/MUM/2006
Oct. 4, 2006   (IN) .................... 1634/MUM/2006

(51) Int. Cl.
*A61P 29/00* (2006.01)
*A61K 31/56* (2006.01)
*C07J 71/00* (2006.01)
(52) U.S. Cl. ......................................... 540/63
(58) Field of Classification Search ............ 540/63
See application file for complete search history.

(56) References Cited

U.S. PATENT DOCUMENTS

| 4,035,369 | A  | 7/1977 | Vandenberk et al. |
| 5,482,934 | A  | 1/1996 | Calatayud et al. |
| 5,728,826 | A  | 3/1998 | Gutterer |
| 6,787,533 | B1 | 9/2004 | Gutterer |
| 2006/0128954 | A1 | 6/2006 | Schmidt |
| 2007/0117974 | A1 | 5/2007 | Ying et al. |

FOREIGN PATENT DOCUMENTS

| CN | 1699395 A | 11/2005 |
| DE | 4129535 A1 | 3/1992 |
| WO | 9524416 A1 | 9/1995 |
| WO | 0238584 A1 | 5/2002 |
| WO | 2004033478 A2 | 4/2004 |
| WO | 2004085460 A1 | 10/2004 |
| WO | 2006138212 A1 | 12/2006 |
| WO | 2008015696 A2 | 2/2008 |
| WO | 2008035066 A2 | 3/2008 |

OTHER PUBLICATIONS

Foreign communication from a priority application—International Preliminary Report on Patentability, PCT/GB2007/003549, Mar. 24, 2009, 14 pages.
Foreign communication from a priority application—International Search Report and Written Opinion, PCT/GB2007/003549, Dec. 11, 2008, 23 pages.
Ying, Minghua, et al., "One-pot process for synthesis of Prednisolone derivatives," abstract of CN 1699395, HCaplus Chemical Abstracts, 2009, 1 page, ACS on STN.

*Primary Examiner* — Brenda Coleman
(74) *Attorney, Agent, or Firm* — Conley Rose, P.C.; Rodney B. Carroll (57) ABSTRACT

Improved processes for the synthesis of ciclesonide, chemically termed as [11β,16α(R)]-16,17-[(cyclohexylmethylene)bis(oxy)]-11-hydroxy-21-(2-methyl-1-oxopropoxy)pregna-1,4-diene-3,20-dione and its crystal modification.

17 Claims, 2 Drawing Sheets

PROCESSES FOR THE PREPARATION OF CICLESONIDE AND ITS CRYSTAL MODIFICATION

CROSS-REFERENCE TO RELATED APPLICATIONS

This application is a national stage entry under 35 U.S.C. §371 of PCT/GB2007/003549, filed Sep. 18, 2007 entitled "Processes for the Preparation of Ciclesonide and Its Crystal Modification," claiming priority of Indian Patent Application Nos. 1634/MUM/2006 filed Oct. 4, 2006 and 1493/MUM/2006 filed Sep. 19, 2006, which applications are incorporated by reference herein in their entirety.

FIELD OF THE INVENTION

The present invention relates to an improved process for the synthesis of ciclesonide, chemically termed as [11β,16α(R)]-16,17-[(cyclohexylmethylene)bis(oxy)]-11-hydroxy-21-(2-methyl-1-oxopropoxy)pregna-1,4-diene-3,20-dione and its crystal modification.

BACKGROUND OF THE INVENTION

[11β,16α(R)]-16,17-[(cyclohexylmethylene)bis(oxy)]-11-hydroxy-21-(2-methyl-1-oxopropoxy) pregna-1,4-diene-3,20-dione also known as ciclesonide is a synthetic corticosteroid and is used to decrease inflammation in the lungs. It was first disclosed in DE4129535 and U.S. Pat. No. 5,482,934.

WO9524416 describes a process for the epimer enrichment of pregna-1,4-diene-3,20-dione 16,17 acetal derivatives by silylation.

U.S. Pat. No. 6,787,533 discloses R-epimer enrichment of 16,17-acetal derivatives of 21-acyloxy pregna-1,4-diene-11β,16α,17α-triol-3,20-dione derivatives.

In all the processes disclosed in the prior art, ciclesonide or its intermediates are subjected to repeated crystallisation for epimer enrichment which leads to loss in yield and makes the processes uneconomical for industrial scale up. In one aspect, the present invention is an attempt to provide a new process for the preparation of [11β,16α(R)]-16,17-[(cyclohexylmethylene)bis (oxy)]-11-hydroxy-21-(2-methyl-1-oxopropoxy)-pregna-1,4-diene-3,20-dione.

Figure 2:
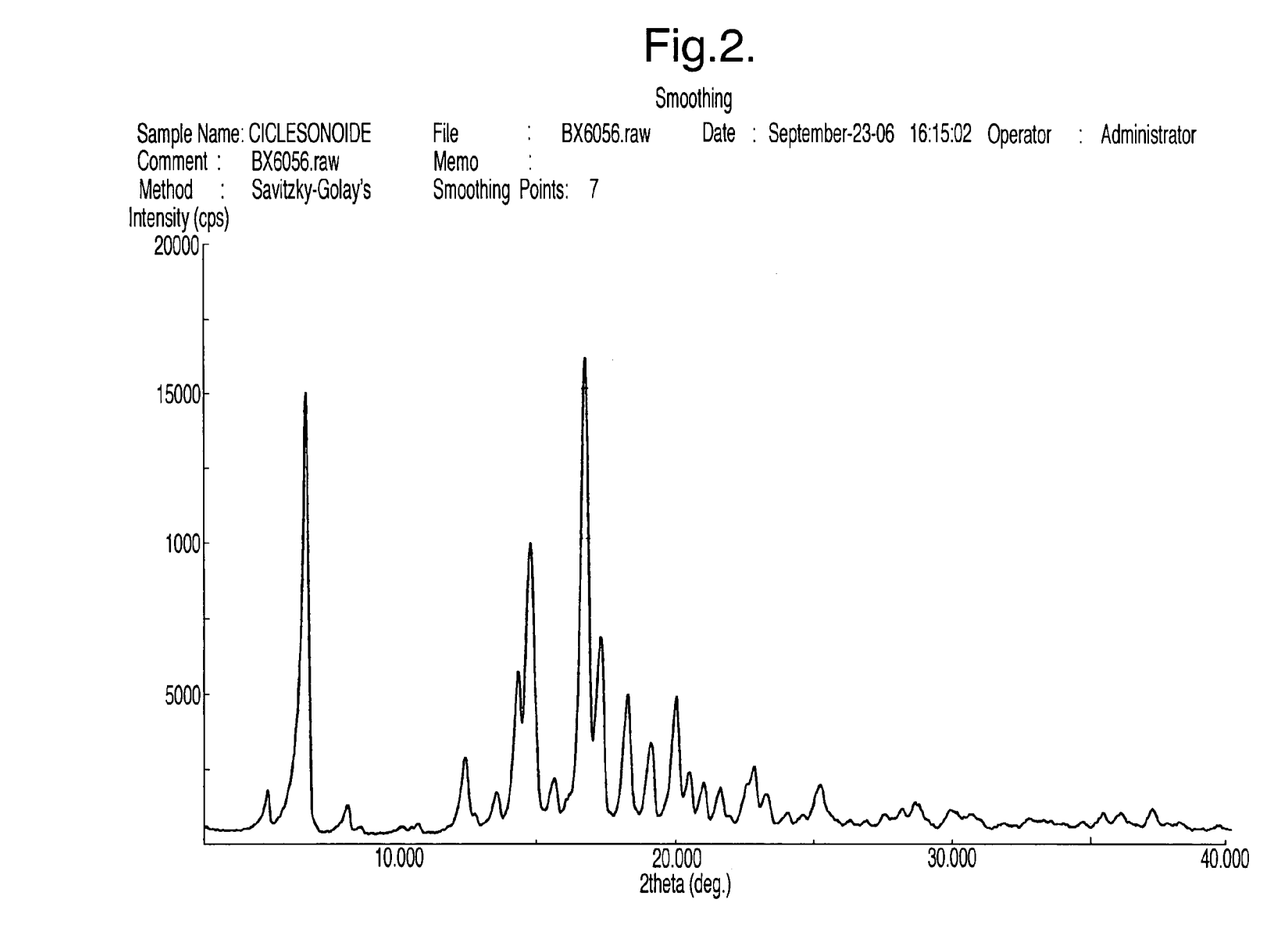
FIG. 2 is an X-ray powder diffraction (XRPD) pattern for ciclesonide Form A.

In the processes of the prior art, ciclesonide is crystallized using a mixture of water and a water miscible solvent. The product thus obtained is in a crystalline form and has an XRD pattern as shown in FIG. 2 and is hereinafter referred to as Form A.

Various crystal modifications of a drug (often referred to as polymorphs) may have substantial differences in physical properties such as particle size hardness. Furthermore, these seemingly-small changes in crystal structure can have a substantially large effect on certain pharmaceutically important properties like dissolution, bioavailability etc. Crystal modifications also include various solvates, hydrates of the drug. Certain drugs have the tendency to form solvates and hydrates.

The existence of a crystal modification of any given compound, which includes solvates and hydrates, cannot be predicted, and there is no standard thumb rule process for preparing a previously unknown crystal modification of a known compound. Even after a crystal modification has been identified, there is no possibility of predicting whether any additional modifications will ever be discovered.

As a result, it would be a landmark contribution in the filed of crystal modification to provide a new crystalline form of ciclesonide, and methods of preparation, pharmaceutical formulations, and methods of use thereof. Also there is further scope and need for an improved process which provides ciclesonide in good yield and purity.

The present invention provides improved processes for the synthesis of ciclesonide which result in ciclesonide having high purity and yield. The present invention further provides a new crystal modification of ciclesonide herein after referred to as Form C and a process for the preparation of Form C.

SUMMARY OF THE INVENTION

According to a first aspect of the present invention, there is provided a process for preparing a compound of formula B comprising reacting a compound of formula A wherein R is H or a protecting group, with a metabisulfite complex of formula 2 wherein X is an alkali metal, in the presence of an acid and a solvent. In an embodiment, R is —C(O)R', wherein R' is a C1 to C6 straight chain or branched chain alkyl group. Preferably, R' is methyl. Alternatively, R' may be ethyl, n-propyl, isopropyl, n-butyl, isobutyl, t-butyl, n-pentyl, n-hexyl or the like. In another embodiment, R' is —CH(CH$_3$)$_2$ and the compound of formula B is ciclesonide. Thus, the present invention provides the direct synthesis of ciclesonide from the compound of formula A when R' is —CH(CH$_3$)$_2$. In an embodiment, X is potassium or sodium, preferably sodium. The acid may be selected from the group consisting of sulphuric acid, acetic acid, formic acid, methane sulphonic acid and perchloric acid, preferably the acid is perchloric acid. The solvent may be an organic solvent. For example, the solvent may be selected from the group consisting of dichloroethane, acetonitrile, toluene and dichloromethane, preferably dichloromethane.

In an embodiment where R is not —C(O)CH(CH$_3$)$_2$, the process further comprises converting the compound of formula B to ciclesonide. For example, when R is a protecting group, the conversion comprises converting the —OR group to a hydroxy group and converting the hydroxy group to a —OC(O)CH(CH$_3$)$_2$ group. In an embodiment, R is —C(O)R' and the conversion of —OR to a hydroxy group comprises hydrolysis. The conversion of formula B to ciclesonide may be by any process known from the prior art, for example, the step of converting the hydroxy group to a —OC(O)CH(CH$_3$)$_2$ group may be carried out in the presence of isobutyric anhydride. Alternatively, the step of converting the hydroxy group to a —OC(O)CH(CH$_3$)$_2$ group is carried out in the presence of isobutyryl chloride. In another embodiment, the metabisulfite complex of formula 2 is prepared according to the process described in the third aspect below.

According to a second aspect of the present invention, there is provided a cyclohexane carboxaldehyde metabisulfite complex having the formula 2

2 wherein X is an alkali metal. In an embodiment, X is potassium or sodium. Preferably, X is sodium.

According to a third aspect of the present invention, there is provided a process for preparing a metabisulfite complex having the formula 2 as defined above, the process comprising reacting cyclohexane carboxaldehyde with the corresponding alkali metal metabisulfite having the formula X$_2$S$_2$O$_5$. The process may be carried out in the presence of water and a solvent. In an embodiment, the solvent is denatured ethanol. For example, the ethanol may be denatured with acetone or toluene.

According to a fourth aspect of the present invention, there is provided the use of a cyclohexane carboxaldehyde metabisulfite complex as defined above in the preparation of ciclesonide.

According to a fifth aspect of the present invention, there is provided a process for preparing a compound of formula B

B

A comprising reacting a compound of formula A wherein R is a protecting group, with cyclohexane carboxaldehyde in the presence of an acid and a solvent. In an embodiment, the solvent is a water miscible solvent or a mixture of a chlorinated solvent and a water miscible organic solvent. In an embodiment, R is —C(O)R', wherein R' is a C1 to C6 straight chain or branched chain alkyl group. Preferably, R' is methyl. Alternatively, R' may be ethyl, n-propyl, isopropyl, n-butyl, isobutyl, t-butyl, n-pentyl, n-hexyl or the like. Suitably, the acid is an organic or inorganic acid. For example, the acid may be selected from the group consisting of sulphuric acid, acetic acid, formic acid, methane sulphonic acid and perchloric acid. Preferably, the acid is perchloric acid. Optionally, the chlorinated solvent is selected from the group consisting of dichloromethane, dichloroethane, chloroform or mixtures thereof. Suitably, the water miscible solvent is selected from the group consisting of tetrahydrofuran, acetonitrile, C1 to C4 alcohols, acetone or mixtures thereof. A preferred mixture of solvents is dichloromethane and acetonitrile.

In an embodiment, R' is —CH(CH$_3$)$_2$ and the compound of formula B is ciclesonide. Thus, the present invention provides the direct synthesis of ciclesonide from the compound of formula A when R' is —CH(CH$_3$)$_2$.

In another embodiment, R is not —C(O)CH(CH$_3$)$_2$, and the process further comprises converting the compound of formula B to ciclesonide. Suitably, the conversion comprises converting the —OR group to a hydroxy group and converting the hydroxy group to a group having the formula —OC(O)CH(CH$_3$)$_2$. In an embodiment. R is —C(O)R' and the conversion of —OR to hydroxy comprises hydrolysis. Optionally, the step of converting the hydroxy group to a —OC(O)CH(CH$_3$)$_2$ group is carried out in the presence of isobutyric anhydride.

According to a sixth aspect of the present invention, there is provided a process for preparing ciclesonide comprising reacting a compound of formula B wherein R is H, with isobutyryl chloride in the presence of an organic base and an organic solvent. Suitably, the base is selected from the group consisting of pyridine, dimethyl amino pyridine, piperidine and a trialkyl amine. Preferably, the trialkylamine is triethylamine. Optionally, the organic solvent is a chlorinated solvent, such as dichloromethane. The compound of formula B may be prepared in any of the ways described above in the first and fifth aspects of the present invention.

According to a seventh aspect of the present invention, there is provided a process for purifying ciclesonide comprising crystallising or recrystallising the ciclesonide from methanol. For example, if the crude ciclesonide is not isolated as a solid, it may be in situ crystallised from methanol. Alternatively, if the crude ciclesonide is isolated as a solid, it may be recrystallised from methanol. The ciclesonide used for purification may be prepared according to any one of the processes described above in the first, fifth and sixth aspects of the present invention. The purified ciclesonide may be in the form of crystalline methanol solvate Form C.

According to an eighth aspect of the present invention, there is provided compound A wherein R is a protecting group, with the proviso that R is not —C(O)CH$_3$, i.e. 16α-hydroxy prednisilone 21 acetate. In an embodiment, R is —C(O)R', wherein R' is a C1 to C6 straight chain or branched chain alkyl group. R' may be ethyl, n-propyl, isopropyl, n-butyl, isobutyl, t-butyl, n-pentyl, n-hexyl or the like. Optionally, R' is —CH(CH$_3$)$_2$.

According to a ninth aspect of the present invention, there is provided compound B wherein R is a protecting group, with the proviso that R is not —C(O)CH(CH$_3$)$_2$. In an embodiment, R is —C(O)R', wherein R' is a C1 to C6 straight chain or branched chain alkyl group. Optionally, R' is methyl. Alternatively, R' may be ethyl, n-propyl, isopropyl, n-butyl, isobutyl, t-butyl, n-pentyl, n-hexyl or the like.

According to a further aspect of the present invention, there is provided crystalline ciclesonide methanol solvate Form C. In an embodiment, the methanol content ranges from 1% to 10%. Crystalline ciclesonide methanol solvate Form C may be characterised as having an X-ray powder diffraction pattern with characteristic peaks at 8.7, 15.9 and 18.2° 2θ±0.2° 2θ. Form C may have an X-ray powder diffraction pattern with further characteristic peaks at 13.1, 15.2 and 26.2° 2θ±0.2° 2θ. Form C have an X-ray powder diffraction pattern with still further characteristic peaks at 10.5, 11.8, 12.9, 17.6 and 24.7° 2θ±0.2° 2θ. Crystalline ciclesonide methanol solvate Form C may have an X-ray diffractogram, or substantially the same X-ray diffractogram, as set out in FIG. 1.

According to a further aspect of the present invention, there is provided a process for preparing anhydrous crystalline ciclesonide Form A comprising desolvating crystalline ciclesonide methanol solvate Form C.

In an embodiment, crystalline ciclesonide methanol solvate Form C is stirred in water for a period of time ranging from 1 hour to 6 hours to form a suspension, followed by cooling and isolating solid crystalline anhydrous ciclesonide Form A. Suitably, the stirring takes place at a temperature ranging from 50 to 60° C. Optionally, the isolated solid is dried in a vacuum oven at a temperature above 60° C., more preferably above 90° C.

In another embodiment, crystalline ciclesonide methanol solvate Form C is stirred in an anti-solvent at a temperature ranging from 25° C. to 60° C. for a period of time ranging from 2 hours to 12 hours to form a suspension followed by cooling and isolating solid crystalline anhydrous ciclesonide Form A. Suitably, the suspension is cooled to a temperature below 25° C., preferably to a temperature ranging from 0 to 10° C. The solid may be dried under vacuum, preferably at 90° C. The anti-solvent may be selected from the group consisting of hexane, heptane, toluene, xylene, acetonitrile, ethyl acetate, acetone, methyl isobutyl ketone and diisopropyl ether.

Ciclesonide prepared according to any one of the processes described above forms another aspect of the present invention.

According to a further aspect of the present invention, there is provided a pharmaceutical composition comprising ciclesonide as described above, together with one or more pharmaceutically acceptable excipients.

The present invention also provides the use of ciclesonide as described above in medicine. The present invention further provides the use of ciclesonide as described above in the manufacture of a medicament for decreasing inflammation in the lungs. Still further, the present invention provides a method of decreasing inflammation in the lungs in a patient in need thereof comprising administering to said patient ciclesonide as described above.

DETAILED DESCRIPTION

In one aspect, the present invention provides a process for the synthesis of an intermediate useful in the formation of [11β,16α(R)]-16,17-[(cyclohexylmethylene)bis(oxy)]-11-hydroxy-21-(2-methyl-1-oxopropoxy)-pregna-1,4-diene-3,20-dione, the synthesis involving the use of a novel adduct, more particularly using a metabisulphite adduct of cyclohexane carboxaldehyde.

Cyclohexane carboxaldehyde has been used as an intermediate for the synthesis of [11β,16α(R)]-16,17-[(cyclohexylmethylene)bis(oxy)]-11-hydroxy-21-(2-methyl-1-oxopropoxy)pregna-1,4-diene-3,20-dione Cyclohexane carboxaldehyde is an unstable compound and is not available in pure form. Cyclohexane carboxaldehyde when used as such for the synthesis generates many impurities and affords the product in low yield.

It is known in the art that some aldehydes can be purified by converting them into a metabisulphite complex and then breaking the complex to obtain the purified aldehyde. Surprisingly it has been found that, not only can cyclohexane carboxaldehyde be purified by converting it into a stable metabisulphite adduct, but also that the adduct can be directly reacted with 11β,16α,17α-21-tetrahydroxy-pregna-1,4-diene-3,20-dione; there is no need to break the adduct and isolate the aldehyde. This process generates fewer impurities and gives the product in good yield. The adduct may also be reacted with the corresponding 21 isobutyryl compound (i.e. the compound of formula A, wherein R is —C(O)CH(CH₃)₂) to yield ciclesonide directly. This process is very convenient as it does not involve the additional step of converting the 21 hydroxy group to the isobutyryl group. Consequently, such a process results in an even higher yield ciclesonide product.

In another aspect, the present invention provides a process for preparing the cyclohexane carboxaldehyde metabisulphite complex which comprises reacting cyclohexane carboxaldehyde dissolved in a solvent, such as denatured industrial sprit with a solution of an alkali metal metabisulfite, for example sodium metabisulphite, in water. The resulting precipitate may be isolated by filtration, washing with industrial spirit and drying in a vacuum oven to obtain the complex.

In an embodiment, the present invention provides an improved process for the synthesis of [11β,16α(R)]-16,17-[(cyclohexylmethylene)bis(oxy)]-11-hydroxy-21-(2-methyl-1-oxopropoxy)pregna-1,4-diene-3,20-dione (C) as shown in Scheme 1 below which comprises reacting sodium metabisulphite complex (2) with 11β,16α,17α,21-tetrahydroxy-pregna-1,4-diene-3,20-dione (A), in the presence of perchloric acid using a suitable solvent, preferably dichloromethane, to give the compound of formula (B). Compound (B) is further reacted with isobutyryl chloride using an organic base, preferably triethylamine, in a suitable organic solvent to give [11β,16α(R)]-16,17-[(cyclohexylmethylene)bis(oxy)]-11-hydroxy-21-(2-methyl-1-oxopropoxy)-pregna-1,4-diene-3,20-dione which is isolated and recrystallised from methanol.

In another embodiment, the present invention provides an improved process for the synthesis of [11β,16α(R)]-16,17-[(cyclohexylmethylene)bis(oxy)]-11-hydroxy-21-(2-methyl-1-oxopropoxy)pregna-1,4-diene-3,20-dione (C) as shown in Scheme 2 below content can be further enhanced to 99% and above by crystallisation or recrystallisation using methanol.

In another embodiment, the present invention provides a process for preparing ciclesonide wherein a protected form of 11β,16α,17α,21-tetrahydroxypregna-1,4-diene-3,20-dione (A) (protected at the 21 position) is reacted with cyclohexane carboxaldehyde in the presence of an organic or inorganic acid like sulphuric acid, acetic acid, formic acid, methane sulphonic acid, preferably perchloric acid using a mixture of chlorinated solvent and a water miscible organic solvent. The which comprises reacting sodium metabisulphite complex (2) with 11β,16α,17α-trihydroxy-21-acetate-pregna-1,4-diene-3,20-dione (D) in the presence of perchloric acid using a suitable solvent, preferably dichloromethane, to give a compound of formula (E). Compound (E) is further hydrolysed to give (B) which is reacted with isobutyryl chloride to give [11β,16α(R)]-16,17-[(cyclohexylmethylene)bis(oxy)]-11-hydroxy-21-(2-methyl-1-oxopropoxy)-pregna-1,4-diene-3,20-dione (C) which is isolated and recrystallised from methanol.

The process of the present invention surprisingly provides ciclesonide in an enriched form wherein the proportion of the desired R-epimer is greater than 96%.

Surprisingly, it has been found that using the reaction conditions of the present invention, in particular the metabisulfite adduct, ciclesonide can be isolated directly from the reaction mass, wherein the R-epimer is greater than 96%. This epimer purity is achieved without resorting to any of the extensive/repeated crystallisations disclosed in the prior art. The epimer reaction was also performed using only a water miscible organic solvent at temperature ranging from 0 to 25-30° C. to give compound of formula (B). The chlorinated solvent used may comprise dichloromethane, dichloroethane, chloroform or mixtures thereof, and the water miscible solvent used may comprise tetrahydrofuran, acetonitrile, C1-C4 alcohols, acetone or mixtures thereof. Compound (B) may be further reacted with isobutyryl chloride using an organic base, preferably triethylamine, in a suitable organic solvent to give [11β,16α(R)]-16,17-[(cyclohexylmethylene)bis(oxy)]-11-hydroxy-21-(2-methyl-1-oxopropoxy)-pregna-1,4-diene-3,20-dione which is isolated from methanol and has an R-epimer content greater than 96%.

In yet another embodiment, the present invention further provides an improved process for the synthesis of [11β,16α(R)]-16,17-[(cyclohexylmethylene)bis(oxy)]-11-hydroxy-21-(2-methyl-1-oxopropoxy)-pregna-1,4-diene-3,20-dione (C) as shown in Scheme 3, which comprises reacting cyclohexane carboxaldehyde with 11β,16α17α-trihydroxy-21-acetate-pregna-1,4-diene-3,20-dione (D) in the presence of an organic or inorganic acid, such as sulphuric acid, acetic acid, formic acid, or methane sulphonic acid, preferably perchloric acid, using a mixture of a chlorinated solvent and a water miscible organic solvent or only in presence of a water miscible organic to give compound of formula (E). Compound (E) may be further reacted with isobutyryl chloride to give [11β,16α(R)]-16,17-[(cyclohexylmethylene)bis(oxy)]-11-hydroxy-21-(2-methyl-1-oxopropoxy)-pregna-1,4-diene-3,20-dione (C) which is isolated from methanol and optionally crystallized from methanol.

During the experimentation for the present invention, it was found that ciclesonide has the tendency to form solvates with C1 to C4 alcohols. Ciclesonide when isolated from methanol forms needle shaped crystals in the form of a methanol solvate, which is hereinafter termed as crystal modification Form C. Thus another aspect, the present invention provides a new crystal modification of ciclesonide (Form C).

The advantage of isolating ciclesonide from the reaction in the form of a solvate is that it is free from the impurities formed during the reaction, and also the ciclesonide is obtained in an enriched form with respect to its epimeric Scheme 3

Typically, 11β,16α,17α,21-tetrahydroxy-1,4-pregna-diene-3,20-dione (A) is reacted with cyclohexane carboxaldehyde in the presence of an organic or inorganic acid like sulphuric acid, acetic acid, formic acid, methane sulphonic acid, preferably perchloric acid using a mixture of chlorinated solvent and a water miscible organic solvent at a temperature ranging from 0 to 30° C., preferably 0 to 25° C. to give the compound of formula (B). The compound (B) may be further reacted with isobutyryl chloride in the presence of an organic base, preferably triethylamine, and the product may be isolated from methanol. Ciclesonide may be further recrystallized with methanol to obtain ciclesonide having the proportion of R-epimer greater than 99%.

The processes of the present invention for preparing ciclesonide do not have to involve the isolation of intermediate (B), and, when intermediate (B) is not isolated, yield loss is avoided during the isolation of (B), which thus provides ciclesonide in good yields.

purity: ciclesonide methanol solvate has an epimeric purity preferably more than 96%. The methanol content of the ciclesonide methanol solvate ranges from about 1 to 10%.

The methanol solvate may be desolvated by stirring in water, preferably at a temperature ranging from 50 to 60° C. for a period of time ranging from 1 to 6 hrs. The suspension may then be cooled and the solid filtered and dried in a vacuum oven, preferably at a temperature above 60° C., more preferably above 90° C. to obtain crystalline anhydrous ciclesonide free from any residual solvent.

The methanol solvate ciclesonide may also be desolvated by stirring in an anti-solvent at a temperature ranging from 25° C. to 60° C. for a period of time ranging from 2 hrs. to 12 hrs. The suspension may then be cooled to a temperature below 25° C., preferably to a temperature ranging from 0 to 10° C. and filtered. The wet solid may be dried under vacuum, preferably at 90° C. The anti-solvent used may be selected from the group consisting of hexane, heptane, toluene, xylene, acetonitrile, ethyl acetate, acetone, methyl isobutyl ketone and diisopropyl ether. After desolvating, the ciclesonide is isolated as an anhydrous crystalline form Form A.

Thus, a process for preparing anhydrous crystalline ciclesonide Form A from an alcohol solvate forms another aspect of the present invention.

Figure 1:
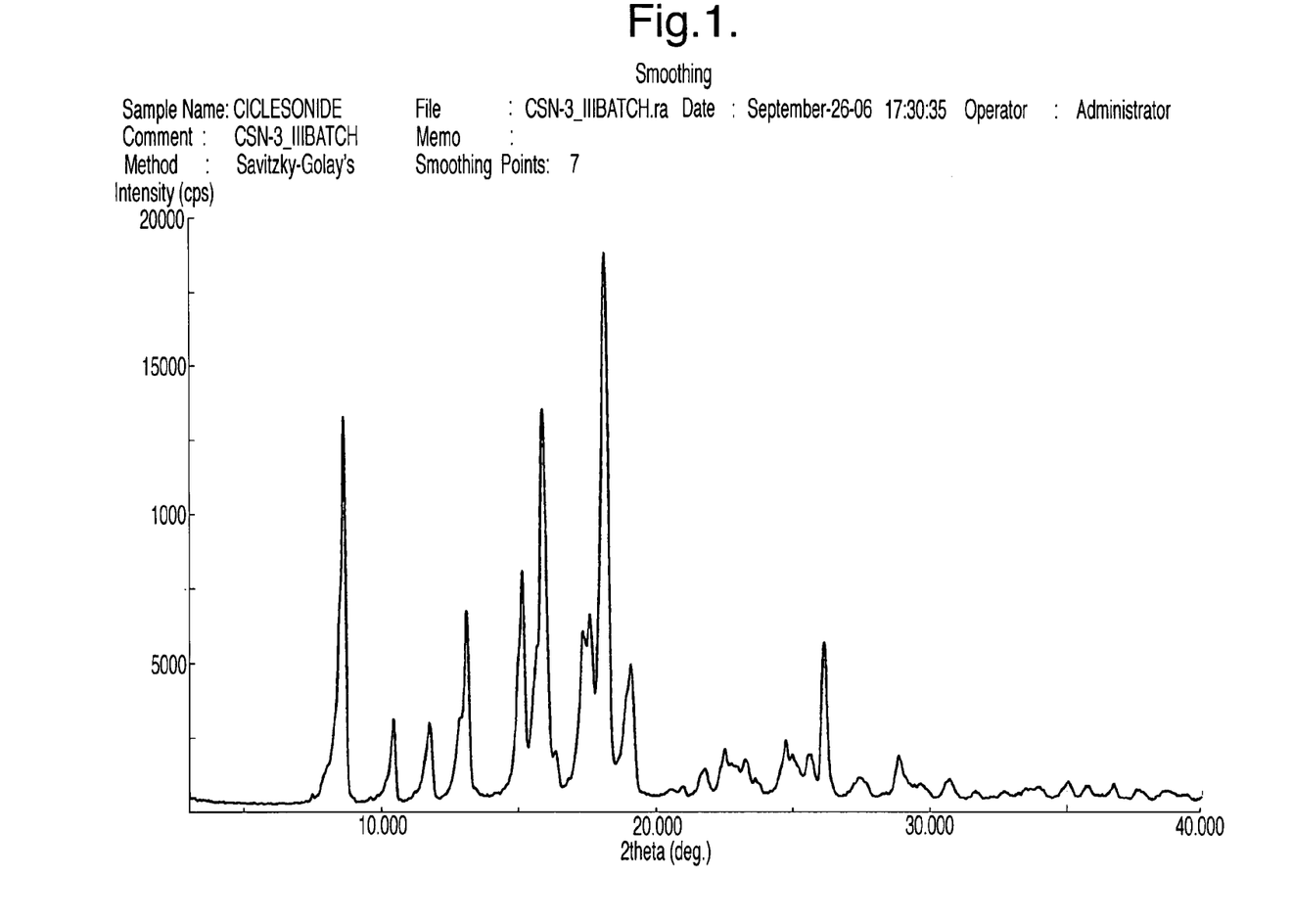
FIG. 1 is an X-ray powder diffraction (XRPD) pattern for ciclesonide Form C.

Ciclesonide Form C of the present invention is further characterized by the X-ray powder diffraction spectrum shown in FIG. 1, where the vertical axis is intensity and the horizontal axis is the 2θ angle, in degrees.

The XRPD of the ciclesonide Form C was measured on a Rigaku miniflex advance powder X-ray Powder Diffractometer using a Cu K alpha-1 radiation source, and is characterized by its X-Ray powder diffraction spectrum having peaks (±0.2° 2θ) as expressed in Table 1.

TABLE 1

| Diffraction angles (2θ°) | Relative Intensity (I/I$_o$) |
|---|---|
| 8.7 | 76.3 |
| 10.5 | 16.3 |
| 11.8 | 15.3 |
| 12.9 | 15.5 |
| 13.1 | 37.0 |
| 15.2 | 44.3 |
| 15.9 | 74.3 |
| 17.6 | 32.6 |
| 18.2 | 100 |
| 24.7 | 8.3 |
| 26.2 | 30.6 |

EXAMPLES

The invention is further described by reference to the following examples, which set forth in detail certain aspects and embodiments of the preparation of compounds and compositions of the present invention. It will be apparent to those skilled in the art, that many modifications, both to materials and methods, can be practiced without departing from the purpose and intent of this invention. The examples that follow are not intended to limit the scope of the invention as described hereinabove or as claimed below.

Example 1

Preparation of Cyclohexane Carboxaldehyde Metabisulphite Complex 100 gms of cyclohexane carboxaldehyde was dissolved in 400 ml of industrial spirit (denatured ethanol) and a solution of sodium metabisulphite (95 gms) in water (150 ml) was added under stirring. The resulting precipitate was filtered and washed with industrial spirit and dried under vacuum at a temperature of about 50-60° C. to obtain 150 gms of the titled complex having 99.5% purity.

Example 2

Preparation of 11β,16α-(R,S)-16,17-[(cyclohexylmethylene)bis(oxy)]11,21-dihydroxy-pregna-1,4-diene-3,20-dione (B)

100 gm of 16α-hydroxy prednisolone (A) was suspended in 2.0 lt dichloromethane and treated with 200 ml of 70% perchloric acid. 50 gms of cyclohexane carboxaldehyde metabisulphite complex (2) was added in lots maintaining a temperature between 0 and 5° C. The reaction mass was stirred at 0 to 5° C. for 6 hrs and then neutralized with 10% sodium bicarbonate solution. The organic phase was separated and dried using sodium sulphate. The organic phase was concentrated under vacuum to obtain a residue which was stripped with 100 ml methanol. The solvent was concentrated and the residue was dissolved by refluxing in methanol. The clear solution was cooled to 25 to 30° C. and the resulting solid was filtered under vacuum to obtain 80 gm. of the titled compound. (Epimer ratio R:S=97.5:2.5)

Example 3

Preparation of 11β,16α-(R,S)-16,17-[(cyclohexylmethylene)bis(oxy)]11-hydroxy-21-(2-methyl-1-oxo-propoxy)-pregna-1,4-diene-3,20-dione (C)-Ciclesonide 25 gm of 11β,16α-(R,S)-16,17-[(cyclohexylmethylene)bis(oxy)]11,21-dihydroxy-pregna-1,4-diene-3,20-dione (B) were suspended in 250 ml dichloromethane at 25 to 30 C. The reaction mass was chilled to 0 to 5° C., and 12.8 ml triethyl amine was added followed by 10.0 ml isobutyryl chloride diluted in 125 ml dichloromethane which was added slowly at 0 to 5° C. over a period of 30 min. The reaction mass was diluted with 400 ml water, the organic layer was separated and washed with water, dried over sodium sulphate and concentrated under vacuum to obtain a residue. The residue was dissolved by refluxing in 100 ml methanol. The clear solution was chilled to 10 to 15° C. and filtered. The product was dried under vacuum at 90° C. to obtain 25 gm of the title compound. If required the product is recrystallised from methanol to obtain the desired epimer ratio R:S=99.7:0.3.

Example 4

Preparation of 11β,16α-(R,S)-16,17-[(cyclohexylmethylene)bis(oxy)]11-hydroxy-pregna-1,4-diene-3,20-dione, 21-acetate (E)

75 gm of 11β,16α,17α-trihydroxy pregna-1,4-diene-3,20-dione, 21-acetate (D) were suspended in 1.0 lt dichloromethane and treated with 100 ml of 70% perchloric acid. 30 gms of cyclohexane carboxaldehyde metabisulphite complex (2) was added in lots maintaining a temperature between 0 and 5° C. The reaction mass was stirred at 0 to 5° C. for 6 hrs and then neutralized with 10% sodium bicarbonate solution. The organic phase was separated and concentrated under vacuum to residue. Methanol was added and the resulting suspension was stirred for 1 hr., filtered and dried under vacuum to obtain 65 gm. of the title compound (Epimer ratio R:S=94:6).

Example 5

Preparation of 11β,16α-(R,S)-16,17-[(cyclohexylmethylene)bis(oxy)]11,21-dihydroxy-pregna-1,4diene-3,20-dione (B)

33 gm of 11β,16α-(R,S)-16,17-[(cyclohexylmethylene)bis(oxy)]11-hydroxy-pregna-1,4-diene-3,20-dione, 21-acetate (E) was suspended in 330 ml methanol and 165 ml dichloromethane under nitrogen atmosphere to obtain a clear solution. The reaction was cooled to between 0 and 5° C. and 1.32 gm potassium hydroxide was added while maintaining the temperature between 0 and 5° C. and further stirred for 1 hr. The solution was neutralized using dilute acetic acid (pH 6.0-7.0) and concentrated in vacuum to obtain a thick slurry. 70 ml methanol was added and the suspension was heated to 50° C. and stirred for 1 hr. and later cooled to between 0 and 5° C. and filtered to obtain 25 gm of the title compound. (Epimer ratio R:S=95:5)

Example 6

Preparation of 11β,16α-(R,S)-16,17-[(cyclohexylmethylene)bis(oxy)]-11,21-dihydroxy-pregna-1,4-diene-3,20-dione (B)

11β,16α,17α-21-tetrahydroxypregna-1,4-diene-3,20-dione (A) (100 gms) was charged in a mixture of dichloromethane (1.0 ltr.) and acetonitrile (1.0 ltr.) and cooled to 0° C. Perchloric acid (400 ml) was added to the reaction mass at 0 to 5° C. followed by cyclohexane carboxaldehyde (40 ml) and stirred at 0 to 5° C. for 4 to 5 hrs. After reaction completion, 10% sodium bicarbonate solution (2.0 ltrs) was added under stiffing. The dichloromethane layer was separated and washed with water and dried using sodium sulphate. The solvent was concentrated under vacuum below 50° C. to residue. The residue was dissolved in methanol (300 ml) and stirred at 25 to 30° C. for 2 hrs. The product was filtered and dried under vacuum at 70° C. to give 90 gms. of (B) (Epimer Ratio R:S=90:10).

Example 7

Preparation of 11β,16α-(R,S)-16,17-[(cyclohexylmethylene)bis(oxy)]11-hydroxy-21-(2-methyl-1-oxopropoxy)-pregna-1,4-diene-3,20-dione (1)-Ciclesonide 50 gm of 11β,16α-(R,S)-16,17-[(cyclohexylmethylene)bis(oxy)]-11,21-dihydroxy-pregna-1,4-diene-3,20-dione (B) was suspended in 500 ml of dichloromethane at 25° C. The suspension was chilled to 0 to 5° C., and 26 ml triethyl amine was added. 20.0 ml isobutyryl chloride diluted with 250 ml dichloromethane was added slowly at 0 to 5° C. over a period of 30 mins. After reaction completion, the reaction mass was diluted with 800 ml water, and the organic layer was separated and washed with water. The organic layer was dried using sodium sulphate and concentrated under vacuum to obtain a residue. The residue was refluxed in 200 ml methanol to obtain a clear solution. The clear solution was chilled to 0 to 5° C. and stirred for 1 hr and filtered, washed with chilled methanol and dried under vacuum to obtain 40 gm of the pure product having epimer ratio (R:S=99.62:0.38.) The solid obtained was identified as a methanol solvate (Form C) and characterised by powder X-ray diffraction.

Example 8

Desolvation of Form C

Ciclesonide methanol solvate 100 gms (Form C) was suspended in 1.0 lt. of water and the suspension was stirred and heated at 50 to 60° C. for 2 hrs. The suspension was cooled to 25 to 30° C. The solid was filtered and washed with water and dried under vacuum at 90° C. for 6 hrs. to obtain 96 gms of anhydrous crystalline ciclesonide (Form A).

Example 9

Preparation of 11β,16α-(R,S)-16,17-[(cyclohexylmethylene)bis(oxy)]11-hydroxy-pregna-1,4-diene-3, 20-dione, 21-acetate (E)

50 gm of 11β,16α,17α,trihydroxypregna-1,4-diene-3,20-dione, 21-acetate (D) was suspended in 1.0 lt of dichloromethane and treated with 75 ml of 70% perchloric acid and then chilled to 0 to 5° C. 20 ml of cyclohexane carboxaldehyde was added dropwise maintaining the temperature between 0 and 5° C. After stirring at 0 to 5° C. for 6 hrs, the reaction mass was neutralized with 10% sodium bicarbonate solution. The organic phase was separated and dried using sodium sulphate, and the organic phase was concentrated under vacuum to obtain an oil which was stirred in di-isopropyl ether. The resulting solid was filtered and dried to obtain 44 gm of the crude product having epimer ratio as R:S=92:8. The crude product was dissolved in 88 ml methanol at 70° C. and the clear solution was chilled to 0 to 5° C. and the resulting solids were filtered and washed with methanol and dried under vacuum to obtain 36 gm of pure titled compound (epimer ratio as R:S=96:4).

Example 10

Preparation of 11β,16α-(R,S)-16,17-[(cyclohexylmethylene)bis(oxy)]-11,21-dihydroxy-pregna-1,4-diene-3,20-dione (B)

50 gm of 11β,16α-(R,S)-16,17-[(cyclohexylmethylene)bis(oxy)]-11-hydroxy-pregna-1,4-diene-3,20-dione, 21-acetate (E) was suspended in 400 ml methanol and 200 ml dichloromethane under nitrogen atmosphere to obtain a clear solution. The reaction mass was cooled and 1.32 gm potassium hydroxide was added and stirred for 1 hr. The solution was neutralized with dilute acetic acid (pH-6.0-7.0) and concentrated in vacuum to obtain a thick slurry. The product was then dissolved in methanol at 50° C. and later chilled to 0- to 5° C., filtered and dried to obtain 35 gm (Epimer ratio R:S=98:2).

Example 11

Preparation of 11β,16α-(R,S)-16,17-[(cyclohexylmethylene)bis(oxy)]-11-hydroxy-21-(2-methyl-1-oxopropoxy)-pregna-1,4diene-3,20-dione (1)-Ciclesonide 100 gm, of 11β,16α-(R,S)-16,17-[(cyclohexylmethylene)bis(oxy)]-11,21-dihydroxy-pregna-1,4-diene-3,20-dione (B) was suspended in 1000 ml of dichloromethane at 25° C. and chilled to 0 to 5° C. 50 ml triethyl amine was added. 40.0 ml isobutyryl chloride diluted with 500 ml dichloromethane was added slowly at 0 to 5° C. over a period of 30 mins. After reaction completion, the reaction mass was diluted with 1500 ml water, the organic layer was separated and washed with water. The organic layer was dried using sodium sulphate and concentrated under vacuum to a residue. The residue was refluxed in 500 ml methanol to obtain a clear solution. The clear solution was chilled to 0 to 5° C., stirred for 1 hr and filtered. The wet cake was stirred in 200 ml of diisopropyl ether for 1 hr. and filtered. The solid obtained was dried under vacuum at 90° C. to obtain 80 gms of pure anhydrous crystalline ciclesonide (Form A). (Epimer ratio as R:S=99.7:0.3)

Example 12

Preparation of 11β,16α-(R,S)-16,17-[(cyclohexylmethylene)bis(oxy)]-11-hydroxy-21-(2-methyl-1-oxopropoxy)-pregna-1,4diene-3,20-dione (1)-Ciclesonide 11β,16α,17α-trihydroxypregna-21-(2-methyl-1-oxopropoxy)1,4-diene-3,20-dione (100 gms) was charged in a mixture of dichloromethane (1.0 ltr.) and acetonitrile (1.0 ltr.) and cooled to 0° C. Perchloric acid (400 ml) was added to the reaction mass at 0 to 5° C. followed by cyclohexane carboxaldehyde (40 ml) and stirred at 0 to 5° C. for 4 to 5 hrs. After reaction completion, 10% sodium bicarbonate solution (2.0 ltrs) was added under stirring. The dichloromethane layer was separated and washed with water and dried using sodium sulphate. The solvent was concentrated under vacuum below 50° C. to residue. The residue was dissolved in methanol (300 ml) and stirred at 25 to 30° C. for 2 hrs. The product was filtered, recrystallized from methanol and dried under vacuum at 50° C. to give 90 gms. of (1) (Epimer Ratio R:S=98:2).

It will be appreciated that the invention may be modified within the scope of the appended claims.

The invention claimed is:

1. A process for preparing a compound of formula B

B comprising reacting a compound of formula A

A wherein R is —C(O)R', wherein R' is a C1 to C6 straight chain or branched chain alkyl group, with a metabisulfite complex of formula 2

2 wherein X is an alkali metal, in the presence of an acid and a solvent.

2. The process according to claim 1, wherein R' is methyl.

3. The process according to claim 1, wherein R' is —CH(CH3)2 and the compound of formula B is ciclesonide.

4. The process according to claim 1, wherein the acid is selected from the group consisting of sulphuric acid, acetic acid, formic acid, methane sulphonic acid and perchloric acid.

5. The process according to claim 1, wherein the solvent is selected from the group consisting of dichloroethane, acetonitrile, toluene and dichloromethane.

6. The process according to claim 1, wherein R is not —C(O)CH(CH$_3$)$_2$, further comprising converting the compound of formula B to ciclesonide.

7. The process according to claim 6, wherein converting the compound of formula B to ciclesonide comprises converting the —OR group to a hydroxy group and converting the hydroxy group to a —OC(O)CH(CH$_3$)$_2$ group.

8. The process according to claim 7, wherein conversion of —OR to a hydroxy group comprises hydrolysis.

9. The process according to claim 7, wherein the step of converting the hydroxy group to a —OC(O)CH(CH$_3$)$_2$ group is carried out in the presence of isobutyric anhydride or isobutyryl chloride.

10. A method comprising utilizing a cyclohexane carboxaldehyde metabisulfite complex having the formula 2

2 wherein X is an alkali metal in the preparation of ciclesonide.

11. A process for preparing a compound of formula B comprising reacting a compound of formula A wherein R is —C(O)R', wherein R' is a C1 to C6 straight chain or branched chain alkyl group, with cyclohexane carboxaldehyde in the presence of an acid and a solvent.

12. A process for preparing ciclesonide comprising reacting a compound of formula B wherein R is H, with isobutyryl chloride in the presence of an organic base and an organic solvent.

13. The process according to claim 12, wherein the base is selected from the group consisting of pyridine, dimethylaminopyridine, piperidine and a trialkylamine.

14. The process according to claim 12, wherein the organic solvent is a chlorinated solvent.

15. A process for purifying ciclesonide comprising crystallising or recrystallising the ciclesonide from methanol.

16. Crystalline ciclesonide methanol solvate Form C.

17. A process for preparing anhydrous crystalline ciclesonide Form A comprising desolvating crystalline ciclesonide methanol solvate Form C.

* * * * *